United States Patent [19]

Liu et al.

[11] Patent Number: 5,916,544
[45] Date of Patent: Jun. 29, 1999

[54] SUNSCREEN CONCENTRATE

[75] Inventors: Kou-Chang Liu, Wayne; Michael Helioff, Westfield; Mark Rerek, Scotch Plains, all of N.J.; Mary Davis, Suffern, N.Y.; Lawrence J. Grenner, Glen Rock, N.J.; David E. Graham, Surrey, United Kingdom; Anja Waldorf-Geber, Königswinter; Renate Koppel, Köln, both of Germany

[73] Assignee: ISP Investments Inc., Wilmington, Del.

[21] Appl. No.: 08/968,171

[22] Filed: Nov. 12, 1997

[51] Int. Cl.$^6$ .................... A61K 7/42; A61K 7/44; A61K 6/00; A61K 7/00
[52] U.S. Cl. .................... 424/59; 424/60; 424/401
[58] Field of Search .................... 424/401, 59, 60

[56] References Cited

U.S. PATENT DOCUMENTS

| | | | |
|---|---|---|---|
| 4,893,729 | 1/1990 | Iggulden et al. | 222/42 |
| 5,417,961 | 5/1995 | Nearn et al. | 424/59 |
| 5,445,815 | 8/1995 | Siegfried | 424/59 |
| 5,597,574 | 1/1997 | Narayanan et al. | 424/401 |
| 5,817,298 | 10/1998 | Galley et al. | 424/59 |

*Primary Examiner*—Shelley A. Dodson
*Assistant Examiner*—Marina Lamm
*Attorney, Agent, or Firm*—William J. Davis; Walter Katz; Marilyn J. Maue

[57] ABSTRACT

A sunscreen concentrate in the form of a stable, uniform dispersion comprising, by weight:

(a) about 30–65% of ultrafine titanium dioxide or zinc oxide, or mixtures thereof, (b) about 30–70% of an organic sunscreen agent, and (c) about 0.25–25% of a dispersing aid which is polyvinylpyrrolidone alkylated with a $C_4$–$C_{36}$ alpha-olefin.

16 Claims, No Drawings

SUNSCREEN CONCENTRATE

BACKGROUND OF THE INVENTION

1. Field of the Invention

This invention relates to a sunscreen composition, and, more particularly, to a stable, uniform dispersion of ultrafine titanium dioxide or zinc oxide in an organic sunscreen agent with polyvinylpyrrolidone alkylated with an alpha-olefin as a dispersing aid.

2. Description of the Prior Art

Sunscreen compositions have been described extensively in the prior art. See, for example, U.S. Pat. Nos. 4,810,489; 4,820,508; 5,026,540; 5,041,281; 5,207,998; 5,219,559; 5,306,485; 5,445,815; 5,508,024; 5,599,529; and 5,603,863. Such compositions usually are formulated by admixing the several components in predetermined amounts. However, disadvantageously, such admixing often requires an elaborate sequence of addition of each of the components in expensive mixing equipment and order to assure a homogeneously dispersed composition.

Accordingly, it is an object of this invention to provide a sunscreen concentrate in the form of a stable, homogeneous dispersion from which a sunscreen composition can be formed readily by simple dilution with a carrier.

Another object of the invention is to provide a sunscreen concentrate comprising a stable, homogeneous dispersion of ultrafine titanium dioxide or zinc oxide, in an organic sunscreen agent, with polyvinylpyrrolidone alkylated with an alpha-olefin as a dispersing aid.

Still another object herein is to provide a waterproofing sunscreen concentrate having both an inorganic sunblock agent and a UV-absorbing organic sunscreen agent therein, in a hydrophilic or hydrophobic copolymer of polyvinylpyrrolidone and an alpha-olefin, wherein the particle size (u, microns) of the concentrate is about $0.01-0.2\mu$, preferably about $0.05-0.1\mu$, and a Brookfield viscosity of about 4,000 to 1,000,000 cps, preferably about 5,000 to 400,000 cps.

These and other objects and features of the invention will be made apparent from the following more detailed description of the invention.

SUMMARY OF THE INVENTION

What is described herein is a waterproofing sunscreen concentrate in the form of a stable, uniform dispersion comprising, by weight:

(a) about 30–65% of ultrafine titanium dioxide or zinc oxide, or mixtures thereof, (b) about 30–70% of an organic sunscreen agent, and (c) about 0.25–25% of a dispersing aid which is polyvinylpyrrolidone alkylated with a $C_4$–$C_{36}$ alpha-olefin.

Suitably, the particle size of the concentrate is about $0.01-0.2\mu$, preferably about $0.05-0.1\mu$; and the Brookfield viscosity is about 4,000 to 1,000,000 cps, preferably 5,000 to 400,000 cps.

Commercial sunscreen compositions may be prepared easily by mixing the sunscreen concentrate of the invention with water and other conventional ingredients of such compositions.

DETAILED DESCRIPTION OF THE INVENTION

The waterproofing sunscreen concentrate of the invention includes a sunblock component (a) which is ultrafine titaniumn dioxide or zinc oxide, present in an amount of about 30–65% by weight of the concentrate. Ultrafine titanium dioxide is preferred.

The sunscreen concentrate of the invention also includes an UV-absorbing sunscreen agent which is the active component (b). Suitable organic sunscreen agents include cinoxate(2-ethoxyethyl-p-methoxycinnamate); diethanolamine-p-methoxycinnamate; digalloyl trioleate ethyl 4-bis(hydroxypropyl)aminobenzoate; ethylhexyl-p-methoxy-cinnamate; 2-ethylhexyl salicylate; glyceryl aminobenzoate; homosalate(3,3,5-trimethylcyclohexyl salicylate); triethanolamine salicylate; 2-phenyl-benzimidazole-5-sulfonic acid; sulisobenzone(2-hydroxy-4-methoxybenzophenone-5-sulfonic acid); Padimate A (amyl p-dimethylaminobenzoate); Padimate O (octyl dimethyl para aminobenzoate); and menthyl anthranilate, and mixtures thereof.

The sunscreen agents also may include a sunscreen material particulary suitable for ultraviolet-A (320–400 nm) protection. This compound suitably is selected from oxybenzone, dioxybenzone; 2-ethylhexyl-2-cyano-3,3 diphenylacrylate; methyl benzilidine camphor; 4-t-butyl-4'-methoxydibenzoyl-methane and mixtures thereof.

The total amount of organic sunscreen agent suitably is present in an amount ranging from about 30% to 70%, preferably about 35–55%, by weight of the total concentrate.

Component (c) of the sunscreen concentrate of the invention is a dispersing aid to provide the concentrate as a stable uniform dispersion. The dispersing aid herein is polyvinylpyrrolidone (PVP) alkylated with a $C_4$–$C_{36}$ alpha-olefin; suitably present in an amount of about 0.25 to 25% by weight of the concentrate. Component (c) may be a hydrophilic or hydrophobic polymer. A hydrophilic copolymer is made by grafting a $C_4$ alpha-olefin upon the PVP; it is sold by International Specialty Products Inc. (ISP), as Ganex® P-904LC and P-904. The hydrophilic copolymer suitably is present in the concentrate in an amount of about 0.25–4%, preferably about 0.5–2%, by weight of the concentrate. Hydrophobic copolymers are made by grafting a $C_{16}$ to $C_{36}$ alpha-olefin upon PVP. These hydrophobic copolymers also are available from ISP as Ganex® V-216, a liquid, or Ganex® V-220 and WP 660, which are available in the form of waxy solids or flakes. Ganex® V-216 suitably is present in the concentrate in an amount of about 0.25–25%, and optimally 5–20%, while Ganex® V-220 suitably is present in an amount of about 5–25%, preferably 10–20%. A preferred hydrophobic copolymer is Ganex® V-216. A $C_{20}$ alpha-olefin containing copolymer preferably is present in an amount of about 5–25%.

The sunscreen concentrate of the invention may be formed by simply mixing components (a), (b) and (c), using conventional, inexpensive agitation equipment. The sunscreen concentrate thus formed is a stable, homogeneous dispersion of an inorganic sunblock, an organic sunscreen agent, and a Ganex® dispersion aid, having a particle size of about $0.01-0.2\mu$, preferably $0.05-0.1\mu$, and a Brookfield viscosity of 4,000 to 1,000,000 cps, preferably about 5,000 to 400,000 cps.

Thereafter, upon simple dilution of the sunscreen concentrate with an appropriate carrier, and other adjuvants, if desired, an end-use broad spectrum waterproofing sunscreen composition can be readily prepared which can provide a uniform distribution of active sunblock and sunscreen agents upon the skin of the user at selected SPF values.

The invention will now be illustrated by the following working examples.

EXAMPLE 1

An organic sunscreen solution was prepared by dissolving 100 g of Ganex V-216 in 200 g of Escalol® 557 with the aid of a homogenizer. Then 500 g of 2 mm zirconium silicate beads were introduced into a Sand Mill vessel and enough of the solution was added to cover the beads. Then 200 g of Kemira® UV-Titan M-262 ultrafine titanium dioxide was slowly added to the zirconium beads. The mill was run for 4 hours, and the zirconium beads were filtered off. A white dispersion was obtained having a Brookfield viscosity of 6040 cps (Helipath, spindle TB @ 10 rpm)

EXAMPLE 2–16

Following the procedure of Example 1, the following dispersion systems were prepared.

EXAMPLE 2

A white dispersion of
Ganex V-216—75 g
Escalol 557—225 g
UF $TiO_2$, Kemira UV Titan M262—200 g with a Brookfield viscosity of 7800 cps (spindle TB @ 10 rpm).

EXAMPLE 3

A white dispersion of
Ganex V-216—50 g
Escalol 557—250 g
UF $TiO_2$, Kemira UV Titan M262—200 g with a Brookfield viscosity of 16,200 cps (spindle TB @ 10 rpm).

EXAMPLE 4

A white dispersion of
Ganex V-216—25 g
Escalol 557—275 g
UF $TiO_2$, Kemira UV Titan M262—200 g with a Brookfield viscosity of 22,600 cps (spindle TB @ 10 rpm).

EXAMPLE 5

A white dispersion of
Ganex V-216—10 g
Escalol 557—290 g
UF $TiO_2$, Kemira UV Titan M262—200 g with a Brookfield viscosity of 21,900 cps (spindle TB @ 10 rpm).

EXAMPLE 6

A white dispersion of
Ganex V-216—5 g
Escalol 557—295 g
UF $TiO_2$, Kemira UV Titan M262—200 g with a Brookfield viscosity of 25,200 cps (spindle TB @ 10 rpm).

EXAMPLE 7

The procedure of Example 1 was followed using 6.28 g of Ganex V-216 in 119 g of Escalol 557, 314 g of 2 mm zirconium silicate beads, titanium dioxide and 94.5 g of Finex 25 ultrafine zinc oxide. A white dispersion with a Brookfield viscosity of 28,000 cps (spindle TC @ 10 rpm) was obtained.

EXAMPLE 8

A white dispersion of
Ganex V-216—5 g
Escalol 557—295 g
UF $TiO_2$, Tayca SMT-100 SAS—200 g with a Brookfield viscosity of 83,000 cps (spindle TC @ 10 rpm).

EXAMPLE 9

A white dispersion of
Ganex V-216—6 g
Escalol 557—354 g
UF $TiO_2$, Kemira UV-X161—240 g with a Brookfield viscosity of 256,000 cps (spindle TE @ 10 rpm).

EXAMPLE 10

A light beige dispersion of
Ganex V-216—6 g
Escalol 557—380 g
UF $TiO_2$, Tayca MT-100T—240 g with a Brookfield viscosity of 302,000 cps (spindle TE @ 10 rpm).

EXAMPLE 11

A white dispersion of
Ganex P-904—5 g
Escalol 557—295 g
UF $TiO_2$, Kemira UV-Titan M-262—200 g with a Brookfield viscosity of 104,000 cps (spindle TE @ 10 rpm).

EXAMPLE 12

A light beige dispersion of
Ganex P-904—5 g
Escalol 557—295 g
UF $TiO_2$, Tayca MT-100T—200 g with a Brookfield viscosity of 334,000 cps (spindle TE @ 10 rpm).

EXAMPLE 13

A paste of
Ganex V-220—100 g
Escalol 557—250 g
UF $TiO_2$, Kemira UV-Titan M-262—200 g
The dispersion was a paste.

EXAMPLE 14

A white dispersion of
Ganex P-904—12 g
Escalol 557—348 g
UF ZnO, Z-Cote HP-1—240 g with a Brookfield viscosity of 12,000 cps (spindle TB @ 10 rpm).

EXAMPLE 15

A white dispersion of
Ganex V-516—12 g
Escalol 557—348 g
UF $TiO_2$, Kemira UV-Titan M-262—240 g with a Brookfield viscosity of 84,400 cps (spindle TD @ 10 rpm).

EXAMPLE 16

A white dispersion of
Ganex WP-660—18 g
Escalol 557—402 g
UF $TiO_2$, Tayca MT-100T—180 g with a Brookfield viscosity of 142,000 cps (spindle TE @ 10 rpm).

TABLE

DISPERSION COMPOSITIONS OF EXAMPLES 1–16

| Ingredients | % By wt. | Brookfield Viscosity |
|---|---|---|
| Example 1 | | |
| Ganex V-216 | 20 | |
| Escalol 557 | 40 | |
| Kemira M262 | 40 | 6040 cps |
| Example 2 | | |
| Ganex V-216 | 15 | |
| Escalol 557 | 45 | |
| Kemira M262 | 40 | 7800 cps |
| Example 3 | | |
| Ganex V-216 | 10 | |
| Escalol 557 | 50 | |
| Kemira M262 | 40 | 16,200 cps |
| Example 4 | | |
| Ganex V-216 | 5 | |
| Escalol 557 | 55 | |
| Kemira M262 | 40 | 22,600 cps |
| Example 5 | | |
| Ganex V-216 | 2 | |
| Escalol 557 | 58 | |
| Kemira M262 | 40 | 21,900 cps |
| Example 6 | | |
| Ganex V-216 | 1 | |
| Escalol 557 | 59 | |
| Kemira M262 | 40 | 25,200 cps |
| Example 7 | | |
| Ganex V-216 | 2 | |
| Escalol 557 | 38 | |
| Kemira M262 ($TiO_2$) | 30 | |
| Finex 25 (ZnO) | 30 | 28,000 cps |
| Example 8 | | |
| Ganex V-216 | 1 | |
| Escalol 557 | 59 | |
| Tayca SMT-100SAS | 40 | 83,000 cps |
| Example 9 | | |
| Ganex V-216 | 1 | |
| Escalol 557 | 59 | |
| Kemira X-161 | 40 | 256,000 cps |
| Example 10 | | |
| Ganex V-216 | 1 | |
| Escalol 557 | 60.7 | |
| Tayca MT 100T | 38.3 | 302,000 cps |
| Example 11 | | |
| Ganex P-904 | 1 | |
| Escalol 557 | 59 | |
| Kemira M262 | 40 | 104,000 cps |
| Example 12 | | |
| Ganex P-904 | 1 | |
| Escalol 557 | 59 | |
| Tayca MT 100T | 40 | 334,000 cps |
| Example 13 | | |
| Ganex V-220 | 18.1 | |
| Escalol 557 | 45.5 | |
| Kemira M262 | 36.4 | Paste |
| Example 14 | | |
| Ganex P-904 | 2 | |
| Escalol 557 | 58 | |
| Z-Cote HP-1 (ZnO) | 40 | 12,000 cps |
| Example 15 | | |
| Ganex V-516 | 2 | |
| Escalol 557 | 58 | |
| Kemira M262 | 40 | 84,400 cps |
| Example 16 | | |
| Ganex WP-660 | 3 | |
| Escalol 557 | 67 | |
| Tayca MT 100T | 30 | 142,000 cps |

PREPARATION OF SUNSCREEN CONCENTRATE OF INVENTION

EXAMPLE 17

A stable, uniform dispersion of the sunscreen concentrate of the invention was prepared by mixing ultrafine titanium dioxide (Kemira UV Titan M262, Tayca MT-100T or Tayca SMT-100 SAS), (240 g, 40 wt. %), Ganex® P-904 (6 g, 1 wt. %) and Escalol® 557 (357 g, 59 wt. %) as follows:

The Ganex® P-904 and the Escalol® 557 components then were heated to 50° C. with vigorous stirring provided by a Cowles blade affixed to a Premier Dispersator. When the mixture reached 50° C., the ultrafine titanium dioxide powder was slowly introduced into the vortex of the mixture while maintaining its temperature at 50° C. The resultant admixture began to thicken; then agitation was set at 3,000–5,000 rpm, and the batch was stirred continuously for another 15 minutes, then the contents were cooled to room temperature. The resultant dispersion was milled twice through a 3-roll mill. The viscosity of the concentrate as determined in a Brookfield viscometer (Spindle TC, 10 rpm) was 149,000 cps.

PREPARATION OF WATER RESISTANT SUNSCREEN COMPOSITIONS

EXAMPLE 18

| | % By Weight | |
|---|---|---|
| Ingredient | 12A | 12B** |
| Phase A | | |
| Deionized Water | 69.80 | 69.80 |
| V Gum Ultra | 1.00 | 1.00 |
| (Magnesium Aluminum Silicate; Titanium Dioxide; Cristobalite; proprietary substance) | | |
| Glycerine, USP | 1.00 | 1.00 |
| CMC (7H3SF) | 0.50 | 0.50 |
| Phase B | | |
| ProLipid ™ 131 | 3.00 | 3.00 |
| (Stearic Acid (and) Behenyl Alcohol (and) Glyceryl Stearate (and) Maleated Soybean Oil (and) Lecithin (and) $C_{12-16}$ Alcohols (and) Palmitic Acid | | |
| Ceraphyl 791® | 13.50 | 13.50 |
| (Isocetyl Stearoyl Stearate) | | |
| Ceraphyl 847® | 1.00 | 1.00 |
| (Octyldodecyl Stearoyl Stearate) | | |
| *Concentrate of Invention | 10.00 | 10.00 |

-continued

| Ingredient | % By Weight | |
|---|---|---|
| | 12A | 12B** |
| Phase C | | |
| Germall Plus ® (diazolidinyl urea (and) iodopropynyl butylcarbamate) | 0.20 | 0.20 |
| | 100.00 | 100.00 |

*Escalol T {Kemira UV Titan M262 ® 40% + Ganex V-220 @ 20% + Escalol 557 @ 20%}
**Tayca MT100T in Escalol T Procedure Phase A 1. Add the water into an suitable sized vessel depending on the batch size. Begin the mixing while powdering in the V-Gum Ultra. This is done without any heat. Continue mixing until there are no visible signs (beading) of the Gum.

2. At this point you can premix the CMC and glycerin. (It should be noted that the glycerin and CMC should not be made ahead of time, as this mixture thickens up very quickly). While adding in the premix you can begin heating this phase until it reaches a temperature of 75° C.

Phase B

1. Add all of the oil phase ingredients into an appropriate sized vessel with the exception of the titanium dioxide dispersion (Escalol T) which gets added in later. Place the beaker into a water bath and heat until completely melted.

2. Into this add in the titanium dioxide dispersion (Escalol T) and mix until completely dispersed into the oil phase.

3. When the water phase has reached a temperature of 75° C., add in phase B, and continue mixing for about 30 minutes. After 30 minutes homogenize the emulsion for about 5 minutes using the homogenization mode of an Arde Barinco dual mode mixer.

4. Once the emulsion is homogenized you can continue mixing until the batch reaches a temperature of 35° C.–40° C. at which time phase C is added in. Continue mixing until the batch reaches a temperature of 25° C.

5. Check the pH initially and post 24 hours. Measure initial viscosity and post 24 hours.

Physical Characteristics

12A

Initial Viscosity (Brookfield Model RV TDV II, Spindle #4 @ 20 rpm) 7,680 cps

Post 72 hour viscosity (TC spindle @ 10 rpm) 15,580

Initial pH 6.18; post 72 hours 6.24

Rub-in: Not too whitening on rub-out, however, the "waxy" feel of Ganex V-220 creates drag.

12B

Initial Viscosity (Brookfield Model RV TDV II, Spindle #4 @ 20 rpm) 11,300 cps

Post 72 hour viscosity (TC Spindle @ 20 rpm) 22,900 cps

Initial pH 6.0; post 72 hours 5.94

Rub-in: Not too whitening on rub-out, however, the "waxy" feel of Ganex V-220 creates drag.

EXAMPLE 19

| Ingredient | % By Weight | |
|---|---|---|
| | 13A | 13B** |
| Phase A | | |
| Deionized Water | 69.80 | 69.80 |
| V Gum Ultra (Magnesium Aluminum Silicate; Titanium Dioxide; Cristobalite; proprietary substance) | 1.00 | 1.00 |
| Glycerine, USP | 1.00 | 1.00 |
| CMC (7H3SF) | 0.50 | 0.50 |
| Phase B | | |
| ProLipid ™ 131 (Stearic Acid (and) Behenyl Alcohol (and) Glyceryl Stearate (and) Maleated Soybean Oil (and) Lecithin (and) $C_{12-16}$ Alcohols (and) Palmitic Acid | 3.00 | 3.00 |
| Ceraphyl 791 ® (Isocetyl Stearoyl Stearate) | 13.50 | 13.50 |
| Ceraphyl 847 ® (Octyldodecyl Stearoyl Stearate) | 1.00 | 1.00 |
| *Concentrate of Invention | 10.00 | 10.00 |
| Phase C | | |
| Germall Plus ® (diazolidinyl urea (and) iodopropynyl butylcarbamate) | 0.20 | 0.20 |
| | 100.00 | 100.00 |

*Escalol T {Tayca MT100T @ 40% + Ganex V-216 @ 20% + Escalol 557 @ 20%}
**Uses Kemira UV Titan M262 in Escalol T Procedure Phase A 1. Add the water into an suitable sized vessel depending on the batch size. Begin the mixing while powdering in the V-Gum Ultra. This is done without any heat. Continue mixing until there are no visible signs (beading) of the Gum.

2. At this point you can premix the CMC and glycerin. (It should be noted that the glycerin and CMC should not be made ahead of time, as this mixture thickens up very quickly). While adding in the premix you can begin heating this phase until it reaches a temperature of 75° C.

Phase B

1. Add all of the oil phase ingredients into an appropriate sized vessel with the exception of the titanium dioxide dispersion (Escalol T) which gets added in later. Place the beaker into a water bath and heat until completely melted.

2. Into this add in the titanium dioxide dispersion (Escalol T) and mix until completely dispersed into the oil phase.

3. When the water phase has reached a temperature of 75° C., add in phase B, and continue mixing for about 30 minutes. After 30 minutes homogenize the emulsion for about 5 minutes using the homogenization mode of an Arde Barinco dual mode mixer.

4. Once the emulsion is homogenized you can continue mixing until the batch reaches a temperature of 35° C.–40° C. at which time phase C is added in. Continue mixing until the batch reaches a temperature of 25° C.

5. Check the pH initially and post 24 hours. Measure initial viscosity and post 24 hours.

Physical Characteristics

13A

Initial Viscosity (Brookfield Model RV TDV II, TC Spindle @ 10 rpm) 16,300 cps

Post 72 hour viscosity (TC spindle @ 10 rpm) 14,750

Initial pH 5.82; post 72 hours 5.97

Rub-in: Not too whitening on rub-out. Very nice after feel and smooth glossy appearance.

13B

Initial Viscosity (Brookfield Model RV TDV II, TC Spindle @ 10 rpm) 14,800 cps

Post 72 hour viscosity (TC Spindle @ 10 rpm) 15,000 cps

Initial pH 5.97; post 72 hours 6.20

Rub-in: Not too whitening on rub-out. Very nice after feel and smooth glossy appearance.

While the invention has been described with particular reference to certain embodiments thereof, it will be understood that changes and modifications may be made which are within the skill of the art. Accordingly, it is intended to be bound only by the following claims, in which:

What is claimed is:

1. A waterproof sunscreen concentrate in the form of a stable, homogeneous dispersion consisting essentially of, by weight:

(a) about 30–65% of ultrafine titanium dioxide or zinc oxide, or mixtures thereof, (b) about 30–70% of an organic sunscreen agent, (c) about 0.25–25% of a dispersing aid which is a polyvinylpyrrolidone alkylated with a $C_4$–$C_{36}$ alpha-olefin.

2. A sunscreen concentrate according to claim 1 which has a particle size of about 0.01–0.2μ (microns).

3. A sunscreen concentrate according to claim 1 which has a particle size of about 0.05–0.1μ (microns).

4. A sunscreen concentrate according to claim 1 which has a Brookfield viscosity of about 4,000 to 1,000,000 cps.

5. A sunscreen concentrate according to claim 1 which has a Brookfield viscosity of about 5,000 to 400,000 cps.

6. A sunscreen concentrate according to claim 1 wherein (c) is a hydrophilic polymer present in an amount of about 0.25–4%.

7. A sunscreen concentrate according to claim 6 wherein (c) is polyvinylpyrrolidone grafted with a $C_4$ alpha-olefin and is present in an amount of about 0.5–2%.

8. A sunscreen concentrate according to claim 1 wherein (c) is a hydrophobic copolymer present in an amount of about 1–25%.

9. A sunscreen concentrate according to claim 1 wherein (c) is polyvinylpyrrolidone alkylated with a $C_{16}$–$C_{19}$ alpha-olefin, and (c) is present in an amount of about 1–25%.

10. A sunscreen concentrate according to claim 1 wherein (c) is polyvinylpyrrolidone alkylated with a $C_{20}$–$C_{30}$ alpha-olefin, and (c) is present in an amount of 5–25%.

11. A sunscreen concentrate according to claim 1 wherein (a) is present in an amount of 35–60%, (b) is 35–55% and (c) is 5–25%.

12. A sunscreen concentrate according to claim 1 wherein (a) is ultrafine titanium dioxide present in an amount of about 40%, (b) is about 59%, and (c) is a hydrophilic copolymer present in an amount of about 1%.

13. A sunscreen concentrate according to claim 1 wherein component (b) is one or more of the group consisting of oxybenzone(2-hydroxy-4-methoxybenzophenone); dioxybenzone(2,2'-dihydroxy-4-methoxybenzophenone); cinoxate(2-ethoxyethyl-p-methoxycinnamate); diethanolamine-p-methoxycinnamate; digalloyl trioleate ethyl 4-bis(hydroxypropyl)aminobenzoate; 2-ethylhexyl-2-cyano-3,3-diphenylacrylate; ethylhexyl-p-methoxycinnamate; 2-ethylhexyl salicylate; glyceryl aminobenzoate; homosalate(3,3,5-trimethylcyclohexyl salicylate); triethanolamine salicylate; 2-phenylbenzimidazole-5-sulfonic acid; sulisobenzone(2-hydroxy-4-methoxybenzophenone-5-sulfonic acid); Padimate A (amyl p-dimethylaminobenzoate); Padimate O (octyl dimethyl para aminobenzoate); 4-t-butyl-4'-methoxydibenzoylmethane; and the combination of 2-hydroxy-1,4-naphthoquinone with dihydroxyacetone; and menthyl anthranilate, and mixtures thereof; and octyl methoxycinnamate, octacrylene, octyl dimethyl-p-aminobenzoic acid, benzophenone and octyl salicylate, and mixtures thereof.

14. A sunscreen composition comprising the sunscreen concentrate of claim 1, water and optional adjuvants.

15. A sunscreen concentrate according to claim 1 wherein component (b) is ethylhexyl-p-methoxycinnamate.

16. A sunscreen composition according to claim 14 which provides a uniform distribution of component (a) over the skin of the user at different SPF values.

* * * * *